United States Patent [19]
Akinmade

[11] Patent Number: 6,017,982
[45] Date of Patent: Jan. 25, 2000

[54] ORGANIC POLYACID/BASE REACTION CEMENT

[75] Inventor: Ademola Olaseni Akinmade, Calne, United Kingdom

[73] Assignee: BTG International Limited, London, United Kingdom

[21] Appl. No.: 09/124,842

[22] Filed: Jul. 30, 1998

Related U.S. Application Data

[63] Continuation of application No. PCT/GB97/00544, Feb. 26, 1997.
[60] Provisional application No. 60/020,777, Jun. 28, 1996.

[30] Foreign Application Priority Data

Feb. 29, 1996 [GB] United Kingdom .................... 9604342

[51] Int. Cl.[7] ........................................................ C08K 9/00
[52] U.S. Cl. ............................................. 523/216; 106/426
[58] Field of Search ............................... 523/216; 106/426

[56] References Cited

FOREIGN PATENT DOCUMENTS

| | | |
|---|---|---|
| 0 340 016 | 2/1989 | European Pat. Off. . |
| 0 340 016 A2 | 11/1989 | European Pat. Off. . |
| 1139430 | 1/1969 | United Kingdom . |
| 1422337 | 1/1976 | United Kingdom . |
| 2006749 | 5/1979 | United Kingdom . |
| 2029401 | 3/1980 | United Kingdom . |
| 1 587 904 | 4/1981 | United Kingdom . |
| 1 592 882 | 7/1981 | United Kingdom . |
| 2071081 | 9/1981 | United Kingdom . |
| 2107698 | 5/1983 | United Kingdom . |
| 2158431 | 11/1985 | United Kingdom . |
| 2163147 | 2/1986 | United Kingdom . |
| 2 182 044 | 5/1987 | United Kingdom . |
| 2 264 711 | 9/1993 | United Kingdom . |

OTHER PUBLICATIONS

Biomaterials, vol. 15, No. 4, Mar. 1994, Guilford GB, pp. 299,306, XP000451122 M.Darling: "Novel polyakenoate (glass–ionomer) dental cements based on zinc silicate glasses" see p. 299, right–hand col., paragraph, 2–p. 301, left hand col., last paragraph.

*Primary Examiner*—Paul R. Michl
*Attorney, Agent, or Firm*—Nixon & Vanderhye

[57] ABSTRACT

For making a cement such as a dental cement by reacting an organic polyacid (such as polyacrylic acid or polyvinylphosphonic acid or a copolymer of these) with an ion-leachable glass as the base, the invention offers a glass containing the cations Al, Si, Ca and Zn wherein Si:Al>1.5 and Zn is 30–70 percent of those cations. The glass is made by heat treating an aqueous paste of Al, Si, and Ca oxides, such as bentonite, with ZnO and a precursor of ZnO such as zinc acetate, whereby the zinc forms a layer on the glass and is also incorporated as a glass network former. The setting of the cement is speeded and sharpened by using around 2% $MgCl_2$.

24 Claims, No Drawings

ORGANIC POLYACID/BASE REACTION CEMENT

This is a continuation of PCT application PCT/GB97/00544, filed Feb. 26, 1997 and claims benefit of Provisional Appl. Ser. No. 60/020,777 filed Jun. 28, 1996.

This invention relates to an organic polyacid/base reaction cement. Polyalkenoate cements, which are examples of such a cement, contain both carbon-carbon and metal-oxygen bonds. They are employed as dental restorative materials.

The existing classes of polyalkenoate cements are glass-ionomer (e.g. UK Patent GB 1422337) and zinc polycarboxylate (UK Patent GB 1139430). Both of these cements are formed by the neutralisation reaction of polyacids such as poly(acrylic acid), PAA, with calcium alumino silicate and with zinc oxide respectively. Therefore, the cations responsible for the neutralisation reactions are Zn in the case of the former cement and Ca and Al in the case of the glass-ionomer cement. The concept of creating a combination of these two cements is not itself new. An ideal combined polyalkenoate cement would:

i) retain the generic properties of polyalkenoate cements—adhesion and fluoride release;
ii) possess the individual advantages of both the glass-ionomer and zinc polycarboxylate cements;
iii) possess the disadvantages of neither of the cements, viz, for glass-ionomers, poor flexural strength and wear and early susceptibility to water dissolution; for zinc polycarboxylates, poor wetting and low compressive strengths.

Acids other than polyalkenoic acids can be used, instead or alongside, such as poly(vinyl phosphonic acid) or copolymers between poly(carboxylic acid) and poly(vinyl phosphonic acid).

GB-A-2264711 and Darling & Hill, Biomaterials 1994 pp. 299–306 disclose a dental cement made from polycarboxylic acid and a zinc-containing aluminosilicate glass.

Glaschemie, $3^{rd}$ ed., Vogel, pub. Springer 1992, p. 24 discloses a thermometer glass containing $SiO_2$, $B_2O_3$, $Na_2O$, ZnO and $Al_2O_3$.

GB-A-1592882 discloses a dental composition of acrylic and maleic acids and a powder containing $SiO_2$, ZnO, and $Al_2O_3$ and MgO.

EP-A-340016 discloses the production of dental glass ionomer cement using poly(vinyl phosphonic acid) and oxides of Ca, Al and Zn, with $CaF_2$, the ratio Si:Al being 0.6–2.

According to the present invention, a glass comprises, apart from O and F, atoms of Al, Si, Ca and Zn wherein Si:Al>1.5:1, with a zinc oxide layer deposited thereon. Preferably Zn=30–70 e.g. 45–55% of all those atoms apart from O and F. Preferably $Al_2O_3$ <15% by weight of the glass. The glass is preferably in powder form, e.g. finer than 200, more preferably finer than 45 $\mu$m. The glass is preferably ion-leachable and forms a cement with polyalkenoic acid.

The invention thus extends to a pack comprising (i) a water soluble organic polyacid (or mixture) or a hydrolysable precursor thereof, and (ii) a powdered glass as set forth above. The invention further extends to a glass reaction cement made from a glass as set forth above and a polyacid.

Thus, according to the invention, a process for making an organic polyacid/base reaction cement (such as a polyalkenoate cement) comprises mixing an aluminosilicate oxide powder with an aqueous solution comprising polyalkenoic acid, wherein the oxide powder has a layer of zinc oxide deposited on it.

Also according to the invention, there is provided a two-part pack for making an organic polyacid/base reaction cement, comprising an aluminosilicate oxide powder having a layer of zinc oxide deposited on it; organic polyacid (or mixture) or a precursor which forms such an acid upon hydration; and water, wherein the one part contains one of the foregoing constituents and the other part contains the remainder, such that the two parts upon being mixed form a cement. The aluminosilicate oxide can thus be present as an aqueous powdered paste.

Also according to the invention, there is provided an airtight two-part pack for making a polyalkenoate cement, comprising an aluminosilicate oxide powder having a layer of zinc oxide deposited on it, made by heat-treating a mixture of aluminosilicate and zinc oxide constituents or precursors thereof; a polyalkenoic acid or a precursor which forms a polyalkenoic acid upon hydration; and water, wherein the one part contains one of the foregoing constituents and the other part contains the remainder, such that the two parts upon being mixed form a cement.

The oxide preferably further comprises an alkaline earth such as wholly or mainly calcium, preferably in a quantity which would be (at least locally) insufficient by itself to form an acid-degradable glass with the aluminium and silicon, such as 4–15 g (as calcium carbonate) per 100 g of the total oxide.

The oxide powder may be made by heat-treating at e.g. 900–1300° C. (typically 1200° C.) for ¼ to 2 hours a mixture of two or more oxide constituents or precursors thereof, such as zinc oxide, which may accordingly comprise a proportion (e.g. 1–3% preferably 2%) of zinc acetate as a precursor of zinc oxide. The zinc (oxide equivalent) may be present in a proportion of 15 to 70% of the total oxide powder. One of the oxide constituents may be an aluminosilicate clay. The ZnO reacts with $Al_2O_3$ to form $ZnAl_2O_4$ and with $SiO_2$ to form $ZnSi_2O_5$, any ZnO in excess of those stoichiometries remaining as ZnO.

In the preferred heat-treatment range of 1000 to 1200° C., compressive strength (and workable powder:liquid ratios) increase with increasing temperature, and working time and setting time both fall, but at the cost of a worsened (higher) setting time:working time ratio.

Preferably there is also present a chloride salt of a multivalent cation (e.g. $MgCl_2$, $ZnCl_2$, $CaCl_2$, $AlCl_3$), which can speed up the set and sharpen the snap-set effect, preferably in a weight proportion of ½ to 10% (e.g. 1 to 5% such as 1½ to 3%) to the total oxide.

The acid may be a polyalkenoic e.g. poly(carboxylic acid) of molecular weight of the order of $10^4$–$10^6$, such as poly(acrylic acid), e.g. of chain length 75000. In the aqueous solution, the water:polyalkenoic acid weight ratio may be (0.50 to 0.65):1, preferably (0.58 to 0.62):1. In the process and in the two-part pack, the oxide:polyalkenoic acid weight ratio may be (1.10 to 1.50):1, preferably (1.15 to 1.25):1, with the polyalkenoic acid preferably accounting for 32–40%, more preferably 34–38%, of the pack or of the starting mixture in the process. Polyalkenoic acid may be mixed with, copolymerised with, or even replaced by, poly (vinyl phosphonic acid).

Also according to the invention, an air-tight opaque pack for a light-curable cement contains: an aluminosilicate oxide powder having a layer of zinc oxide deposited on it, made by heat-treating a mixture of aluminosilicate and zinc oxide constituents or precursors thereof; fluoride; an aqueous polyalkenoic acid such that in the absence of light and air, the foregoing components equilibrate without setting; a curable resin; a cross-linking monomer; and a light-sensitive initiator.

Also according to the invention, a glass ionomer cement composition comprises an oxide as set forth above, fluoride ions substituting or additional to oxygen in the oxide, and poly(vinyl phosphonic acid).

The oxide usable in the invention will now be described by way of example.

The oxide powder may be regarded as a chemical mixture of polyalkenoate cement formers starting from an ion-(network and modifier) deficient alumino silicate. Zinc ions from organic (e.g. acetate, stearate or oxalate) and inorganic sources are then incorporated into the alumino silicate at elevated temperatures. The suitability of the ion-deficient aluminosilicate is judged primarily by its silica:alumina ratio. For the complete dissociation of the glass network necessary to form practical polyacid reaction cement this ratio must be less than or equal to 3:1. Therefore, for the ion-deficiency criterion to apply In this way, the zinc ions are incorporated in the silicate network as network formers, in the place of the alumina tetrahedra of the glass component of the glass-ionomer cements. Also, excess zinc ions take on the role of network modifiers otherwise assumed by calcium ions in the glass-ionomer cements. The resulting material is acid degradable. It is very versatile in that it possesses variable handling properties (working and setting time and sharpness of set) and mechanical properties. These are dependent on: i) the wide matrix of viable chemical composition; ii) thermal history; and iii) the choice of zinc ions precursor material.

The origin of the aluminosilicate is preferably (but not essentially) the naturally-occurring aluminosilicate, bentonite. Other natural or synthetic silicates with the prerequisite composition will suffice. Bentonite may be partly or wholly replaced by any other montmorillonite or smectite clay mineral, and clay materials based on beidellite, hectorite, sauconite and saponite, and more preferably nontronite, may be used. Admixtures of these with quartz, muscovite, biotite, limonite, hydrous micas, cristobalite, feldspar and vermiculite or volcanic glass may be used. The particle sizes should be mostly in the colloidal range. Attapulgite may be present, as may sepiolite, corrensite, allophane or imogolite. Texas, Arkansas, Mississippi, Kentucky and Tennessee bentonites are preferred to those from Wyoming, South Dakota, Montana, Utah, Nevada and California, which swell in water. The deposition of a layer of zinc oxide, probably from an organic source, on suitable aluminosilicates is a preferred way of putting the invention into effect. Preferably zinc is added as 1 zinc acetate:50–100 zinc oxide by weight. The zinc acetate acts as a precursor of zinc oxide. The zinc compound(s), calcium compound if present and bentonite (or equivalent) are, as powders, mixed in water and the aqueous mixture is fired and if necessary reground. If on the other hand depositing such a zinc oxide layer on glass, there will exist a distinct (if diffuse) bimaterial interface in the acid-degradable particles. In other words, there exists a three dimensional interconnected and interwoven structure of zinc- and calcium-rich aluminosilicates. It is also possible that, added to this, the organic zinc chemicals employed in the cement compositions (e.g. the zinc acetate just mentioned) deposit a thin layer of zinc oxide on the calcium-rich aluminosilicates, separate from and additional to the three-dimensional zinc aluminosilicate.

The invention will now be described by way of example. The compositions of 62 oxides used and of bentonite, glass and "zinc oxide" are as follows:

TABLE 1

The compositions of typical Bentonite, Glass-ionomer Cement Glass and zinc polycarboxylates "zinc oxide" (by weight)

| Components | Bentonite | G338 | "zinc oxide" |
|---|---|---|---|
| Silica | 64.8 | 24.93 | — |
| Alumina | 13.5 | 14.25 | — |
| Calcium oxide | 4.77 | — | — |
| Calcium fluoride | — | 12.82 | — |
| Aluminium phosphate | — | 24.22 | — |

TABLE 1-continued

The compositions of typical Bentonite, Glass-ionomer Cement Glass and zinc polycarboxylates "zinc oxide" (by weight)

| Components | Bentonite | G338 | "zinc oxide" |
|---|---|---|---|
| Cryolite $AlF_3 \cdot 3NaF$ | — | 19.23 | — |
| Aluminium fluoride | — | 4.56 | — |
| Magnesium oxide | 3.63 | — | 17.0 |
| Zinc oxide | — | — | 83.0 |
| Ferric oxide | 1.25 | — | — |
| Sodium oxide | 2.22 | — | — |

The bentonite consisted of granular particles smaller than ¼ mm.
G338 is the designation of a popular commercial glass for glass ionomer cement.

In the following oxide compositions:

1. Calcium carbonate, $CaCO_3$ is used as a cheap and convenient source of calcium oxide (CaO) on firing (note that if CaO itself is used directly, it gives different results, working too fast);

2. ZnAc refers to zinc acetate;

3. The surfactant ("Nansa", trade mark) is needed to dissolve the xanthan gum ("Keltrol", trade mark) in water;

4. Various bentonite grades were used. All samples from Z46 onwards used EXM 622 ADP. The primary distinction between the bentonites is their calcium content-bentonite 0408, EXM 585, EXM 58519 ADP and EXM 622 ADP contain 2, 3, 9 and 5 weight percent calcium respectively. The other oxides can also vary by a few percent, as would be expected from a naturally occurring mineral, as follows:

| Bentonite grade | EX 0408 | EXM 585 | EXM 58519 ADP | EXM 622 ADP |
|---|---|---|---|---|
| X-ray florescence ANALYSIS (%) | | | | |
| $SiO_2$ | 68.6 | 66.8 | 61.7 | 64.8 |
| $TiO_2$ | 0.16 | 0.15 | 0.14 | 0.16 |
| $Al_2O_3$ | 15.4 | 15.0 | 13.8 | 13.5 |
| $Fe_2O_3$ | 1.11 | 1.06 | 1.00 | 1.25 |
| CaO | 2.33 | 3.73 | 9.73 | 4.77 |
| MgO | 3.03 | 2.97 | 2.85 | 3.63 |
| $K_2O$ | 1.26 | 1.18 | 1.10 | 0.32 |
| $Na_2O$ | 2.01 | 1.96 | 1.77 | 2.22 |
| $Mn_3O_4$ | 0.06 | 0.05 | 0.05 | 0.03 |
| $ZrO_2$ | 0.02 | 0.02 | 0.02 | 0.02 |
| SrO | 0.02 | 0.02 | 0.02 | 0.11 |
| Loss on ignition at 1025° C. | 5.85 | 6.60 | 8.00 | 7.61 |
| TOTAL | 99.85 | 99.54 | 100.18 | 98.49 |
| Sulphate | ~0.05% | ~0.05% | ~0.05% | ~1.75% |

The phases present in bentonite of grade EXM 622 ADP are as follows:

montmorillonite—major cristobalite—19% (by volume as determined by X-ray diffraction)

calcite $CaCO_3$—2.1% bassanite $CaSO_4 \cdot \frac{1}{2}H_2O$—5.0%.

COMPONENTS BY WEIGHT

| OXIDE | ZnO | Bentonite | CaCO$_3$ | Xanthan Gum | Surfactant | Water | ZnAc | Firing Regime | Storage Time (days) |
|---|---|---|---|---|---|---|---|---|---|
| Z1  | 50.0 | 30.5 | 16.5 | 0.67 | 0.05 | 150.0 | —    | 1200 C., 120 mins, O  |   |
| Z2  | 50.0 | 30.5 | 16.5 | 0.67 | 0.05 | 150.0 | 1.82 | 1200 C., 120 mins, O  | 8 |
| Z3  | 30.0 | 30.5 | 16.5 | 0.67 | 0.05 | 150.0 | —    | 1200 C., 120 mins, O  | 7 |
| Z4  | 30.0 | 30.5 | 16.5 | 0.67 | 0.05 | 150.0 | 1.37 | 1200 C., 120 mins, O  | 7 |
| Z5  | 70.0 | 30.5 | 16.5 | 0.67 | 0.05 | 150.0 | —    | 1200 C., 120 mins, O  | 7 |
| Z6  | 70.0 | 30.5 | 16.5 | 0.67 | 0.05 | 150.0 | 1.37 | 1200 C., 120 mins, O  | 7 |
| Z7  | 50.0 | 30.5 | 16.5 | 0.67 | 0.05 | 150.0 | 1.82 | 1200 C., 120 mins, RT | 8 |
| Z8  | 30.0 | 30.5 | 16.5 | 0.67 | 0.05 | 150.0 | 1.37 | 1200 C., 120 mins, RT | 7 |
| Z9  | 70.0 | 30.5 | 16.5 | 0.67 | 0.05 | 150.0 | 1.37 | 1200 C., 120 mins, RT | 7 |
| Z10 | 70.0 | 30.5 | 16.5 | 0.67 | 0.05 | 150.0 | 1.37 | 1200 C., 60 mins, RT  | 7 |
| Z11 | 50.0 | 30.5 | 16.5 | 0.67 | 0.05 | 150.0 | —    | 1200 C., 60 mins, RT  | 8 |
| Z12 | 50.0 | 30.5 | 16.5 | 0.67 | 0.05 | 150.0 | 1.82 | 1200 C., 60 mins, RT  | 8 |
| Z13 | 30.0 | 30.5 | 16.5 | 0.67 | 0.05 | 150.0 | —    | 1200 C., 60 mins, RT  | 7 |
| Z14 | 30.0 | 30.5 | 46.5 | 0.67 | 0.05 | 150.0 | 1.37 | 1200 C., 60 mins, RT  | 7 |
| Z15 | 70.0 | 30.5 | 16.5 | 0.67 | 0.05 | 150.0 | —    | 1200 C., 60 mins, RT  | 7 |
| Z20 | 50.0 | 30.5 | 16.5 | 0.67 | 0.05 | 150.0 | 1.82 | 1200 C., 15 mins, RT  | 8 |
| Z21 | 50.0 | 30.5 | 16.5 | 0.67 | 0.05 | 150.0 | 1.82 | 1200 C., 30 mins, RT  | 8 |
| Z24 | 50.0 | 30.5 | 16.5 | 0.67 | 0.05 | 150.0 | —    | 1000 C., 60 mins, RT  | 8 |
| Z25 | 50.0 | 30.5 | 16.5 | 0.67 | 0.05 | 150.0 | —    | 1100 C., 60 mins, RT  | 5 |
| Z26 | 50.0 | 30.5 | 16.5 | 0.67 | 0.05 | 150.0 | 1.21 | 1200 C., 60 mins, RT  | 5 |
| Z27 | 50.0 | 30.5 | 16.5 | 0.67 | 0.05 | 150.0 | 0.60 | 1200 C., 60 mins, RT  | 5 |
| Z28 | 50.0 | 30.5 | 16.5 | 0.67 | 0.05 | 150.0 | 0.60 | 1000 C., 60 mins, RT  | 5 |
| Z29 | 50.0 | 30.5 | 16.5 | 0.67 | 0.05 | 150.0 | 1.21 | 1000 C., 60 mins, RT  | 5 |
| Z30 | 50.0 | 30.5 | 16.5 | 0.67 | 0.05 | 150.0 | 1.82 | 1000 C., 60 mins, RT  | 5 |
| Z3Y | 50.0 | 30.5 | 16.5 | 0.67 | 0.05 | 120.0 | 1.40 | | |
| Z32 | 50.0 | 30.5 | 11.0 | 0.67 | 0.05 | 120.0 | 1.40 | | 7 |
| Z33 | 50.0 | 30.5 | 7.0  | 0.67 | 0.05 | 120.0 | 1.40 | | 8 |
| Z34 | 50.0 | 30.5 | 3.0  | 0.67 | 0.05 | 120.0 | 1.40 | | 8 |
| Z35 | 50.0 | 30.5 | 16.5 | 0.67 | 0.05 | 120.0 | 1.40 | | 7 |
| Z36 | 50.0 | 30.5 | 16.5 | 0.67 | 0.05 | 120.0 | 1.40 | | 7 |
| Z37 | 50.0 | 30.5 | 13.5 | 0.67 | 0.05 | 120.0 | 1.40 | | 7 |
| Z38 | 50.0 | 30.5 | 25.5 | 0.67 | 0.05 | 120.0 | 1.40 | | 8 |
| Z39 | 50.0 | 30.5 | 31.5 | 0.67 | 0.05 | 120.0 | 1.40 | | |
| Z40 | 50.0 | 30.5 | 37.5 | 0.67 | 0.05 | 120.0 | 1.40 | | |

Thus, in oxides Z31–34 and Z37–40, the following respective masses of calcium carbonate were added to 67 g in each case of prefired ZnO+bentonite mix:5.5 g, 3.7 g, 2.3 g, 1.0 g, 6.5 g, 8.5 g, 10.5 g and 12.5 g. In the oxides Z1–Z30, bentonite EXM585 was used. In the oxides Z31–Z44 the bentonite employed is EXO408, while a different batch of EXM585 was used in the oxide Z45. The bentonite EXM622 was employed for the production of the oxides Z46–Z62.

COMPONENTS BY WEIGHT

| OXIDE | ZnO | Bentonite | CaCO$_3$ | Xanthan Gum | Surfactant | Alumina | Water | ZnAc |
|---|---|---|---|---|---|---|---|---|
| Z41 | 50.0  | 30.5  | 16.5 | 0.67 | 0.05  | 4.5  | 120.0 | 1.40 |
| Z42 | 50.0  | 30.5  | 16.5 | 0.67 | 0.05  | 9.0  | 120.0 | 1.40 |
| Z43 | 50.0  | 30.5  | 16.5 | 0.67 | 0.05  | 13.5 | 120.0 | 1.40 |
| Z60 | 150.0 | 61.0  | 33.0 | 1.34 | 0.10  | 27.0 | 240.0 | 2.80 |
| Z44 | 50.0  | 30.5  | 16.5 | 0.67 | 0.05  | 18.0 | 120.0 | 1.40 |
| Z45 | 50.0  | 30.5  | 16.5 | 0.67 | 0.05  | —    | 120.0 | 1.40 |
| Z46 | 16.7  | 10.17 | 5.5  | 0.22 | 0.017 | —    | 40.0  | 0.47 |
| Z47 | 16.7  | 10.17 | —    | 0.22 | 0.017 | 2.2  | 40.0  | 0.47 |
| Z48 | 10.0  | 10.17 | 5.5  | 0.22 | 0.017 | —    | 40.0  | 0.47 |
| Z49 | 3.3   | 10.17 | 5.5  | 0.22 | 0.017 | —    | 40.0  | 0.47 |
| Z50 | 16.7  | 10.17 | 5.5  | 0.22 | 0.017 | 2.2  | 40.0  | 0.47 |
| Z51 | 2.0   | 10.17 | 5.5  | 0.22 | 0.017 | —    | 40.0  | 0.47 |
| Z52 | 1.0   | 10.17 | 5.5  | 0.22 | 0.017 | —    | 40.0  | 0.47 |
| Z53 | 0.5   | 10.17 | 5.5  | 0.22 | 0.017 | —    | 40.0  | 0.47 |
| Z54 | —     | 10.17 | 5.5  | 0.22 | 0.017 | —    | 40.0  | 0.47 |
| Z58 | 16.7  | 10.17 | 1.5  | 0.22 | 0.017 | —    | 40.0  | 0.47 |
| Z59 | 16.7  | 10.17 | 3.5  | 0.22 | 0.017 | —    | 40.0  | 0.47 |
| Z62 | 100.0 | 61.0  | 14.0 | 1.34 | 0.10  | —    | 240.0 | 2.80 |

| COMPONENTS BY WEIGHT | | | | | | | |
|---|---|---|---|---|---|---|---|
| OXIDE | ZnO | ZnF$_2$ | Bentonite | CaF$_2$ | Xanthan Gum | Surfactant | Water | ZnAc |
| Z55 | 16.7 | — | 10.17 | 3.25 | 0.22 | 0.017 | 30.0 | 0.47 |
| Z56 | 8.3 | 10.58 | 10.17 | 3.25 | 0.22 | 0.017 | 40.0 | 0.47 |
| Z57 | — | 21.17 | 10.17 | 4.29 | 0.22 | 0.017 | 40.0 | 0.47 |
| Z61 | — | 127.0 | 61.0 | 25.74 | 1.34 | 0.10 | 240.0 | 2.80 |

Oxide Z57 was found by X-ray diffraction to contain 15 vol % fluorite CaF$_2$, major amounts of willemite ZnSi$_2$O$_4$ and gahnite ZnAl$_2$O$_4$ and a possible trace of grossular Ca$_3$Al$_2$(SiO$_4$)$_3$, and containing 12.2% fluorine.

| COMPONENTS BY WEIGHT | | | | | | |
|---|---|---|---|---|---|---|
| OXIDE | ZnO | G338 (Glass | Xanthan Gum | Surfactant | Water | ZnAc |
| Z16 | 70.0 | 40.0 | 0.67 | 0.05 | 150.0 | — |
| Z17 | 35.0 | 28.0 | 0.33 | 0.025 | 50.0 | — |
| Z18 | 35.0 | 47.0 | 0.33 | 0.025 | 50.0 | — |
| Z19 | 35.0 | 20.0 | 0.33 | 0.025 | 75.0 | 1.5 |

The above oxides were used to form cements.

Composition of cement-forming glasses Z68 and Z69:

| | Z68 | Z69 |
|---|---|---|
| Cement Components (by wt) | | |
| zinc oxide | 15.69 | 12.27 |
| zinc fluoride | 7.49 | 11.65 |
| Bentonite EXM 585 | 13.17 | 13.20 |
| calcium carbonate | 5.18 | 4.11 |
| calcium fluoride | 1.52 | 2.36 |
| alumina | 4.23 | 3.37 |
| zinc acetate | 0.60 | 0.60 |
| Additional components present: - | | |
| water | 51.81 | 51.93 |
| xanthan gum | 0.29 | 0.29 |
| surfactant | 0.002 | 0.002 |

Z68 is the chemical equivalent of physically blending 73 parts by weight of Z60 with 27 parts of Z61 (from which the composition of Z60 can be readily deduced). Z69 is the chemical equivalent of physically blending 58 parts of Z60 with 42 parts of Z61. Physical blends of Z60 and Z61 (in the proportions 73:27 and 58:42 as above) were mixed with water and accelerated with calcium chloride and also with magnesium chloride. Other multivalent water soluble chlorides are also effective. Z68 and Z69 are relatively deactivated by the partial replacement of zinc oxide with zinc fluoride.

Two anhydrous cement powders were prepared: i) 5.0 g of dry poly(acrylic acid) PAA+0.5 g tartaric acid+10.0 g of Z60; ii) 5.0 g of dry PAA+0.5 g of tartaric acid+10.0 g of Z61 (fluoride-containing glass). The anhydrous cement powders were mixed with water at p:w of 3.4:1. This is equivalent to mixing the glasses with a 50% aqueous solution of PAA mediated with 5% tartaric acid.

Various physical blends of the two cement powders were mixed with water at this p:w. In some instances, minute quantities of magnesium chloride hexahydrate were included in the cement powders. The working and setting times of these cements were determined with the aid of Wilson rheometer at 22° C.:

| Description of Anhydrous Cement Powder | Working Time | Setting Time |
|---|---|---|
| 0.34 g of Z60 cement powder | 0.5 | 3.0 |
| 0.30 g Z60 cement + 0.04 g Z61 cement | 2.7 | 6.5 |
| 0.30 g Z60 cement + 0.04 g Z61 cement + 0.006 g MgCl$_2$ | 2.1 | 4.4 |
| 0.25 g Z60 cement + 0.09 g Z61 cement | 2.4 | 7.6 |
| 0.25 g Z60 cement + 0.09 g Z61 cement + 0.01 g MgCl$_2$ | 2.0 | 4.2 |
| 0.20 g Z60 cement + 0.14 g Z61 cement + 0.01 g MgCl$_2$ | 2.1 | 5.6 |

Note: The anhydrous cement powders were mixed with 0.10 g of water.

The cements were formed by mixing the requisite amounts of the oxide powder (P) with liquid (L) being 13% tartaric acid plus 35% E9 poly(acrylic acid) of chain length 75000 PAA aqueous solution—referred to as L1. Cement pastes were introduced into standard stainless steel (6×12) mm moulds, stored for 1 hour dry and then wet for the remainder of the storage period. Their properties are listed in Table 2. A different liquid was used in Table 2A, see later.

In Tables 1, and 3 to 6, O and RT refer to the fired oxide contained in the crucible being left in the furnace overnight, O (after being switched off), and RT (being allowed to equilibrate at room temperature) respectively.

WT(90) refers to the working time, i.e. the time taken for the amplitude of the oscillating rheometer to fall to 90% of its original amplitude. The setting time was the time taken for the amplitude of the rheometer to fall to 5%, ST(5). ZnAc, ZnO and CaCO$_3$ refer to zinc acetate, zinc oxide and calcium carbonate respectively. Bnt refers to the aluminosilicate, bentonite.

TABLE 2

THE PROPERTIES OF THE CEMENTS AT 20° C.

| MATERIAL | COMPRESSIVE STRENGTH (MPa) | FLEXURAL STRENGTH | P:L by weight | WT(90) (mins) | ST(10) (mins) | ST(5) (mins) | ST(5)/WT(90) |
|---|---|---|---|---|---|---|---|
| Z1 | ( ) = Std Deviation | | | 1.0 | 5.4 | 5.8 | 5.8 |
| Z2 | 11.79 (3.13) | | 1.5:1 | | | | |
| Z3 | 12.57 (3.20) | | 1.5:1 | | | | |
| Z4 | 16.36 (1.50) | 7.04 (1.49) | 1.5:1 | | | | |
| Z5 | 16.94 (0.54) | 22.14 (14.09) | 1.5:1 | | | | |
| Z6 | 17.79 (0.30) | 6.41 (1.19) | 1.5:1 | | | | |
| Z7 | 23.91 (1.02) | 11.69 (3.38) | 2.0:1 | 1.8 | 2.8 | 3.0 | 1.7 |
| Z8 | 19.64 (1.53) | 26.76 (3.46) | 2.0:1 | 3.5 | 5.8 | 6.0 | 1.7 |
| Z9 | 22.23 (0.28) | 20.67 (3.46) | 2.0:1 | 2.3 | 5.8 | 6.5 | 2.8 |
| Z10 | 25.05 (1.02) | 23.57 (2.43) | 2.5:1 | 1.9 | 4.0 | 4.4 | 3.8 |
| Z11 | 24.37 (0.91) | 12.74 (2.23) | 2.0:1 | 0.8 | 2.8 | 3.0 | 2.3 |
| Z12 | 22.40 (0.84) | 10.74 (1.06) | 2.5:1 | 2.9 | 6.1 | 6.7 | 2.1 |
| Z13 | 20.54 (0.39) | 11.39 (0.04) | 2.5:1 | 2.5 | 4.8 | 5.2 | 1.7 |
| Z14 | 17.74 (1.04) | 9.00 (2.75) | 2.5:1 | 3.6 | 5.7 | 6.2 | 2.1 |
| Z15 | 24.73 (1.33) | 23.22 (2.74) | 2.5:1 | 2.5 | 4.8 | 5.2 | 4.2 |
| Z20 | 22.30 (1.85) | 32.73 (6.26) | 1.5:1 | 0.7 | 2.7 | 3.0 | |
| Z21 | 26.09 (0.66) | 29.54 (4.63) | −1.5:1 | 4.3 | 6.6 | 7.1 | 1.7 |
| Z24 | 18.76 (2.27) | 24.78 (4.34) | −0.7:1 | 3.7 | 5.6 | 5.9 | 1.6 |
| Z25 | 20.87 (1.30) | 27.55 (3.50) | −1.0:1 | 3.5 | 5.4 | 5.8 | 1.7 |
| Z26 | 24.65 (1.69) | 30.67 (2.95) | −1.8:1 | 3.4 | 6.0 | 6.5 | 1.9 |
| Z27 | 21.11 (4.91) | 18.59 (1.31) | 2.5:1 | 1.9 | 4.8 | 5.4 | 2.8 |
| Z28 | 23.18 (1.40) | 21.51 (3.54) | −1.5:1 | 0.8 | 2.8 | 3.1 | 3.9 |
| Z29 | 24.45 (1.25) | 26.48 (1.47) | −1.5:1 | 1.5 | 3.3 | 3.6 | 2.4 |
| Z30 | 22.40 (1.99) | 24.15 (8.17) | −1.8:1 | 1.4 | 2.4 | 2.5 | 1.8 |
| Z11B | 22.66 (0.91) | | 2.0:1 | 0.8 | 2.8 | 3.0 | 3.8 |
| Z12B | 22.58 (1.26) | | 2.5:1 | 2.9 | 6.1 | 6.7 | 2.3 |

TABLE 2A

| MATERIAL | COMPRESSIVE STRENGTH (MPa) | FLEXURAL STRENGTH | WT(90) (mins) | ST(5) (mins) | ST/WT |
|---|---|---|---|---|---|
| Z21 | 114.56 (8.38) | 29.54 (4.63) | 4.3 | 7.1 | 1.7 |
| Z31 | 141.3 (11.05) | 27.39 (2.77) | 2.9 | 6.1 | 2.1 |
| Z32 | 106.59 (15.30) | 27.57 (3.04) | 1.6 | 2.7 | 1.7 |
| Z33 | 92.84 (9.16) | 33.05 (6.55) | 1.3 | 2.1 | 1.6 |
| Z34 | 80.39 (2.64) | 24.22 (2.35) | 0.8 | 1.5 | 1.9 |
| Z35 | 89.57 (8.20) | — | 3.8 | 8.2 | 2.2 |
| Z36 | 82.58 (20.13) | — | 3.7 | 5.2 | 1.54 |
| Z37 | 120.00 (10.96) | 20.68 (1.82) | 3.2 | 6.0 | 1.9 |
| Z38 | 117.32 (16.69) | 22.95 (2.29) | 3.0 | 6.1 | 2.0 |
| Z39 | 102.33 (7.02) | — | 2.1 | 4.0 | 1.9 |
| Z40 | 68.45 (10.20) | — | 1.7 | 3.9 | 2.3 |
| Z41 | 122.534 (9.60) | 241 (3.28) | 3.5 | 7.3 | 2.1 |
| Z42 | 101.33 (15.91) | 23.87 (5.65) | 3.4 | 6.4 | 1.9 |
| Z43 | 115.83 (13.15) | 20.94 (2.56) | 5.5 | 9.0 | 1.6 |
| Z44 | 121.93 (7.49) | 27.70 (4.61) | 2.7 | 6.3 | 2.3 |
| Z46 | 135.43 (9.73) | 27.70 (2.51) | 3.8 | 6.1 | 1.6 |
| Z47 | 94.27 (2.35) | 25.56 (4.92) | 1.3 | 4.5 | 3.5 |
| Z48 | 122.49 (4.03) | 28.31 (3.27) | 2.8 | 7.0 | 2.5 |
| Z49 | 108.99 (9.31) | 27.98 (3.03) | 2.4 | 6.2 | 2.6 |
| Z50 | 105.74 (1.72) | 28.10 (3.08) | 2.8 | 9.7 | 3.5 |
| Z51 | 98.17 (1.93) | 8.55 (0.71) | 2.5 | 6.5 | 2.6 |
| Z52 | 74.58 (3.12) | 7.39 (0.14) | 2.3 | 8.0 | 3.5 |
| Z53 | 33.07 (2.70) | 2.23 (0.12) | 2.2 | 6.6 | 2.7 |
| Z54 | 14.67 (1.97) | — | — | — | — |
| Z58 | 113.81 (12.20) | 23.20 (2.05) | 1.5 | 4.0 | 2.7 |
| Z59 | 95.50 (12.190) | 21.73 (3.57) | 1.5 | 6.9 | 4.6 |

The flexural strength of Z48 when stored in air at ambient (~40%) humidity was 60 MPa, indicating its usefulness as a splint bandage. (cf plaster of Paris 18 MPa, fibreglass 36 MPa). It is also usefully lighter, the standard sample weighing ½ g (cf plaster of Paris 2½ g, fibreglass 1 g).

TABLE 3

THE EFFECT OF FIRING TIME ON CEMENT PROPERTIES
(Oxides were fired at 1200 C.)

| MATERIAL | FIRING TIME | COMPRESSIVE STRENGTH (MPa) | P:L | WT(90) | ST(10) | ST(5) | ST(5)WT |
|---|---|---|---|---|---|---|---|
| (Z4) | | | | | | | |
| Z4 | 120 mins, O | 16.36 (1.50) | 1.5:1 | | | | |
| Z8 | 120 mins, RT | 19.64 (1.53) | 2.0:1 | 3.5 | 5.8 | 6 | 1.7 |
| Z14 | 60 mins, RT | 17.74 (1.04) | 2.5:1 | 3.6 | 5.7 | 6.2 | 1.7 |
| (Z6) | | | | | | | |
| Z6 | 120 mins, 0 | 17.79 (0.30) | 1.5:1 | | | | |
| Z9 | 120 mins, RT | 22.23 (0.28) | 2.0:1 | 2.3 | 5.8 | 6.5 | 2.8 |
| Z10 | 60 mins, RT | 25.05 (1.02) | 2.5:1 | 1.9 | 4 | 4.4 | 2.3 |
| (Z2) | | | | | | | |
| Z2 | 120 mins, O | 11.179 (3.13) | 1.5:1 | | | | |
| Z7 | 120 mins, RT | 23.9 (1.02) | 2.0:1 | 1.8 | 2.8 | 3 | 1.7 |
| Z12 | 60 mins, RT | 22.40 (0.84) | 2.5:1 | 2.9 | 6.1 | 6.7 | 2.3 |
| Z21 | 30 mins, RT | 26.09 (0.66) | ~1.5:1 | 4.3 | 6.6 | 7.1 | 1.7 |
| Z20 | 15 mins, RT | 22.30 (1.85) | 1.5:1 | 0.7 | 2.7 | 3 | 4.2 |

TABLE 4

THE EFFECT OF ZnO LEVEL ON CEMENT PROPERTIES
(Oxides were fired at 1200 C. for 60 minutes then left at RT)

| OXIDE | ZnO LEVEL | COMPRESSIVE STRENGTH (MPa) | P:L | WT(90) | ST(5) | ST(5)WT(90) |
|---|---|---|---|---|---|---|
| Z11 | 50 g | 24.37 (0.91) | 2.0:1 | 0.8 | 3.0 | 3.8 |
| Z12 | 50 g | 22.40 (0.84) | 2.5:1 | 2.9 | 6.7 | 2.3 |
| Z13 | 30 g | 20.54 (0.39) | 2.5:1 | 2.5 | 5.2 | 2.1 |
| Z14 | 30 g | 17.74 (1.04) | 2.5:1 | 3.6 | 6.2 | 1.7 |
| Z15 | 70 g | 24.73 (1.33) | 2.5:1 | 2.5 | 5.2 | 2.1 |
| Z10 | 70 g | 25.05 (1.02) | 2.5:1 | 1.9 | 4.4 | 2.3 |

TABLE 5

THE EFFECT OF FIRING TEMPERATURE ON CEMENT PROPERTIES
(Oxides were fired for 60 minutes then left at RT)

| OXIDE | FIRING LEVEL | COMPRESSIVE STRENGTH (MPa) | P:L | WT(90) | ST(5) | ST(5)WT(90) |
|---|---|---|---|---|---|---|
| (Z1) | | | | | | |
| Z24 | 1000 C. | 18.76 (2.27) | ~0.7:1 | 3.7 | 5.9 | 1.6 |
| Z25 | 1100 C. | 20.87 (1.30) | ~1.0:1 | 3.5 | 5.8 | 1.7 |
| Z11B | 1200 C. | 22.66 (0.91) | 2.0:1 | 0.8 | 3.0 | 3.8 |

TABLE 6

THE EFFECT OF ZnaC LEVEL ON CEMENT PROPERTIES
(Oxides were fired for 60 minutes then left at RT)

| OXIDE | ZnO LEVEL | COMPRESSIVE STRENGTH (MPa) | P:L | WT(90) | ST(5) | ST(5)WT(90) |
|---|---|---|---|---|---|---|
| 1200 C. | | | | | | |
| Z27 | 1 g | 21.11 (4.91) | 2.5:1 | 1.9 | 5.4 | 2.8 |
| Z26 | 2 g | 24.65 (1.69) | ~1.8:1 | 3.4 | 6.5 | 1.9 |
| Z12B | 3 g | 22.58 (1.26) | 2.5:1 | 2.9 | 6.7 | 2.3 |

TABLE 6-continued

THE EFFECT OF ZnaC LEVEL ON CEMENT PROPERTIES
(Oxides were fired for 60 minutes then left at RT)

| OXIDE | ZnO LEVEL | COMPRESSIVE STRENGTH (MPa) | P:L | WT(90) | ST(5) | ST(5)WT(90) |
|---|---|---|---|---|---|---|
| 1000 C. | | | | | | |
| Z28 | 1 g | 23.18 (1.40) | ~1.5:1 | 0.8 | 3.1 | 3.9 |
| Z29 | 2 g | 24.45 (1.25) | ~1.5:1 | 1.5 | 3.6 | 2.4 |
| Z30 | 3 g | 22.40 (1.99) | ~1.8:1 | 1.4 | 2.5 | 1.8 |

The liquids used in this specification had the following compositions by weight

| | L1 (Table 2) | L2 | L3 | L4 (Table 2A) |
|---|---|---|---|---|
| Poly (acrylic acid) | 35 | 40 | 45 | 50 |
| Tartaric acid | 13 | 13 | 13 | 13 |
| Water | 52 | 47 | 42 | 37 |

These influenced the compressive strength of cement made using Z21 as follows: L1 26 MPa, L2 73 MPa, L3 90 MPa and L4 114½MPa.

An alternative liquid was used in the following test, intended to demonstrate how, as mentioned earlier, Z68 and Z69 are deactivated due to the substitution of zinc oxide by zinc fluoride. The deactivation can be observed by their reaction with poly(acrylic acid) PAA, and with the alternative liquid, a copolymer of acrylic and vinyl phosphonic acid, PVPA/PAA.

Because the fluoride-containing minerals synthesized in this invention, typified by Z61, are more acidic than the traditional basic ion-leachable component of polyalkenoate cements, these fluoride-rich types are not fully decomposed by poly(acrylic acid) to form cements. The use of a stronger polyacid, such as poly(vinyl phosphonic acid), PVPA or the copolymer of vinyl phosphonic acid and acrylic acid as suitable cement formers has been investigated.

The copolymer of vinyl phosphonic acid and acrylic acid (PVPA/PAA) was supplied by A. H. Marks Ltd., Bradford, UK. Two solutions were prepared from the polymers, PVPA/PAA I and PVPA/PAA II:

| | Weight (g) | |
|---|---|---|
| Materials | PVPA/PAA I | PVPA/PAA II |
| PVPA/PAA | 5.00 | 5.00 |
| Dequest D2010 | 0.60 | 1.20 |
| (+) Tartaric acid | 0.60 | — |
| Water | 3.80 | 3.80 |

| | Reactivity with polyacid | |
|---|---|---|
| Glass | PAA | PVPA/PAA |
| Z60 | Fast-setting, but practical | Too reactive |
| Z68 | Slow-setting, but practical especially at high p:l | Too reactive |
| Z69 | Slow-setting, but practical especially at high p:l | Fast-setting, practical at low p:l |
| Z72 | Incomplete reaction, non-practical cements | Fast-setting, practical at wide p:l |

(p:l = powder:liquid ratio)

Properties of the Z68 and Z69 Cements

| Cement Description | | | Compressive | Biaxial Flexural |
|---|---|---|---|---|
| Liquid | p:l | Powder | Strength (MPa) | Strength (MPa) |
| 50% PAA, 15% tartaric acid | 2.5:1 | Z69 | 70.52 (2.98) | 21.99 (1.33) |
| 40% PAA, 15% tartaric acid | 2.5:1 | Z68 | 80.38 (0.62) | 28.87 (1.02) |
| 50% PAA, 15% tartaric acid | 2.0:1 | Z68 | 55.87 (1.52) | 25.44 (2.41) |

Unlike in the case of the reaction of Z61 with poly(acrylic acid) where the cements formed did not set, the cements formed between Z61 and PVPA/PAA set hard within 5 minutes. The compressive and biaxial flexural strengths of cements stored for 24 hours in water at 37° C. were determined:

Properties of the Z61 Cements

| Cement Description | | | Mechanical Properties | |
|---|---|---|---|---|
| | | | Compressive | Biaxial Flexural |
| Powder | Liquid | p:l | Strength (MPa) | Strength (MPa) |
| Z61 | PVPA/PAA I | 3:1 | 133.07 (6.92) | 44.54 (5.17) |
| Z61 | PVPA/PAA II | 3:1 | 135.89 (10.25) | 39.84 (2.55) |

Turning to the effect of fluoride on materials according to the invention, it will be seen that the oxides Z1–Z15, Z20–Z54 and Z58, Z59 do not contain fluoride ions. Z16–Z19 contained fluoride ions introduced in the form of cryolite. Z55 contained calcium fluoride, while Z56 and Z57 contained calcium fluoride and zinc fluoride, at different levels. All the cements formed from fluoride-containing oxides did not set when stored in anaerobic conditions, e.g. in compressive and flexural strength clamps. However, when these cements were exposed to air they set rapidly. They also set when they were heated at elevated temperatures>60C. There are potential applications for these heat- and/or command-curable cements in dentistry, other biomedical fields and the general industrial sector, such as Dentistry:
1. endodontic (root canal) fillers, where physical mixtures of the non-setting cements can be mixed with standard setting-cements to form flexible fluoride-releasing cement replacement for Gutta Percha;
2. one-component temporary filling materials;
3. core build-up/posterior filling materials;
4. specialist adhesive for the bonding of orthodontic bands and brackets and also as a general dental adhesive for bonding crowns, split teeth and endodontic posts;

Biomedical
1. replacement for the existing commercial Plaster of Paris and Fibre-glass splint bandages;
2. replacement for PMMA as a bone cement; and General Industry
1. hard and durable prototype material;
2. household one-component filler for plugging holes and supporting furniture onto walls;
3. roofing material for mending leaks;
4. general repair material for roads and bridges; and
5. component of building blocks and cement material for the construction industry.

As to Biomedical 1 above, commercial splint bandages are made from Plaster of Paris (POP) and resin impregnated with fibre glass. The POP splints are the traditional materials. They are bulky and have high setting exotherms.

The requirements for a splint bandage are:
1) working time, when the cement is manipulable, of 4 minutes at 23° C.;
2) setting time of 5–6 minutes;
3) minimal, preferably negligible setting exotherm;
4) high strength:weight ratio.

A suitable polyalkenoate cement for a splint bandage will comprise three components: acid degradable mineral, tartaric acid and poly(acrylic acid). The tartaric acid may be blended with the mineral and dispersed in acetone, and the dry poly(acrylic acid) may be dissolved in a 9:1 or 19:1 acetone:water mixture.

Blending and dispersion of all the three polyalkenoate cement components, as practised previously, has been found to be deleterious—it leads to premature cement formation during the dispersion process. The obstacle to the use of polyalkenoate cements as a splint bandage material is the inefficient mixing of the cement components when introduced into water, unlike the thorough spatulation of the cements possible on the dental scale to obtain fast-setting dental materials.

The porous foam padding of conventional Plaster of Paris splint bandages was found not to be suitable for the polyalkenoate splint material. It allowed too much polyalkenoate material to leach out upon dipping the splint in water. In the case of the multi-component polyalkenoate cement there is greater need to keep as much of the splint material out of the water as possible. If the foam material is desired to be retained for its comfort, it is preferably covered by a tightly woven fabric, e.g. similar to the fabric covering the other face of a POP splint bandage. This could still be done to leave the foam covering outermost. The polyalkenoate cement can be wrapped in two layers of the conventional light outer cotton fabric. The result has been a reduction in the material leached out and an increase in strength of the resulting splint.

In industrial applications, cheap additives such as specialist sands or furnace slag can be added to the cements to make them more economical. In this way, the cement is only providing the setting reaction, while the added fillers improve the strength of the resulting material.

Cheap additives of this type include salts such as chlorides, nitrates, carbonates are capable of being introduced into the cement system. Chlorides give the benefit of a sharp quick set. Fluorides make the glass more wettable, which allows a higher practical powder:liquid ratio, which gives a stronger product. This is illustrated as follows:

The present fluoride-containing glasses do not form acid/base cements with poly(acrylic acid). However, physical mixtures of these cements set hard when mixed with the standard, non-fluoride-containing glasses. As mentioned earlier, the setting of the resulting cements is speeded up and sharpened by the addition of minute quantities of di- and trivalent chlorides. Magnesium, calcium, zinc and aluminium chlorides can be employed in this way.

Z60 has been tested for its suitability for the bonding of orthodontic brackets. It was tested in stainless steel lap-joints cemented with the following compositions:

| Cement Composition Z60 plus liquid: | Time of Joint Formation | Age of Bonded Joint | Thickness of cement layer (mm) | Bond Strength (MPa) |
| --- | --- | --- | --- | --- |
| 1. 50% PAA, 5% TA, p:l 0.8:1 | 45 seconds | 1 hr | 0.68–0.80 | 4.59 (0.42) |
| 2. 50% PAA, 5% TA, p:l 0.8:1 | 45 seconds | 15 mins | 0.17–0.22 | 5.92 (0.61) |
| 3. 50% PAA, 5% TA, p:l 0.8:1 | 80 second | 15 mins | 0.16–0.65 | 5.97 (0.53) |
| 4. 50% PAA, 5% TA, p:l 0.8:1 | 45 seconds | 24 hours | 0.14–0.51 | 7.87 (0.36) |

PAA and TA refer to poly(acrylic acid) and tartaric acid respectively. "Time of joint formation" refers to the passage of time before the two halves of the lap joint are brought together to sandwich the cement and form a bonded joint. The measurement of this variable is a recognition of the fact that the cementing power of an adhesive diminishes with time (increase in viscosity) as it sets.

A cement with a bond strength of 5.5 MPa is considered likely to be sufficiently robust to maintain the integrity of the bonded brackets under the current clinical procedures.

Thus glasses according to the invention can offer the following properties compared with prior polyalkenoate cements:

| MATERIAL | COMPRESSIVE STRENGTH (MPa) | FLEXURAL STRENGTH (MPa) | SETTING/ WORKING TIMES |
| --- | --- | --- | --- |
| Glass-ionomer | 100–200 | 10–15 | 2.0–3.0 |
| Zinc polycarboxylate | 90–100 | 20–30 | 3.0–4.0 |
| Invention | 70–150 | 20–60 | 1.5–2.5 |

In addition they can be:
1. radio-opaque—a property of the zinc polycarboxylate cements. The glass-ionomer cements are radiolucent;
2. fast-setting. The typical glass-ionomer cement has a ratio of setting:working time of 2–3:1, while the zinc polycarboxylate cement has a ratio of 3–5:1. Some fast-setting cement compositions according to the invention possess setting:working times of 1.5–1–8:1. This is due to the opposing effect of heat on zinc oxide and calcium aluminosilicate—heat deactivates zinc oxide while producing highly strained and reactive glasses;
3. very strong in flexure. This is a reflection of the zinc polyacrylate nature of the matrix of the resulting cements;
4. of high compressive strengths. This is a property normally associated with glass-ionomer cements.
5. less susceptible to early moisture attack. This is due to their relatively modest levels of calcium ions—calcium polyacrylate is soluble in water;
6. less translucent than the glass-ionomer cement but, also, less opaque than the zinc polycarboxylate cements. As in (5) above, this is a reflection of the modest levels of calcium ions in the cements;
7. with fracture properties (fracture toughness and toughness) greater than the existing polyalkenoate cements. This is reflected in their high flexural strengths.
8. a match for the light-activated glass-ionomer cements in mechanical properties, though not in aesthetics. However, they are stronger adhesives (due to the absence of the hydrophobic resins necessary for light activation) and they do not need to be applied and cured in successive thin layers.

The cement as set forth above can be used as a component in a single-paste light cured liner for dental restorative applications. This possibility has been opened by the finding that, with an appropriate proportion of fluoride, the oxide powder set forth above will only partially set in the presence of poly(acrylic acid) and water, reaction appearing to cease at a pH of 3–4. "Cements" formed from these oxides remain putty-like when stored in air-tight tubes. After their initial gelation, the consistency of the "cements" remains stable. With a stronger acid such as poly(vinyl phosphonic acid) or a copolymer of it, such fluoride-containing powders can be made to set.

According to one aspect of this invention, light-curing reagents are added to the components of such partially-formed cements to form a single-paste light cured cement, combining the advantages of strength, adhesion and fluoride release of glass polyalkenoate cement with the command-cure clinical convenience of resin-based cements. This would take the form of an air-tight pack for such a light-curable cement. Some fluoride is essential, such as at least equivalent to 20 mole % or at least 25% of the oxygen, and preferably all the oxygen of the oxide powder is replaced by fluoride. Z55, Z56, Z57, Z61, Z68 and Z69 are examples of fluoride-containing glasses.

The preferred weight ratio of resin: monomer was from 6.5 to 7.5:1. A resin paste formulation, utilising a ratio of 7.47:1, was chosen:

| Material | Weight (%) |
| --- | --- |
| Bis-GMA Resin | 19.53 |
| Urethane Dimethacrylate Resin | 57.09 |
| 1,6-Hexandiol Dimethacrylate (cross-linking monomer) | 10.26 |
| Camphorquinone (light-sensitive initiator) | 13.12 |

The preferred proportion of light-sensitive initiator in a filled restorative cement is from 1 to 5 weight percent of the filled cement. The cements hardened after 40 seconds of light activation.

The preferred proportion of strength-enhancing monomer such as PMDM (pyromellitic dianhydride methacrylate) is up to 4%, preferably 0.5 to 1.5%:

| Material | Weight (g) |
| --- | --- |
| Resin Paste | 1.50 |
| Z61/3 Cement (dried acids + oxide), see later | 1.00 |
| Water | 0.15 |
| R709 Fumed silica filler, see later | 2.50 |
| PMDM | x |

(x = 0 to 0.2, preferably 0.03 to 1, for example ½ g)

Factors that might affect the strength of conventional polyalkenoate cements include: i) the powder:liquid ratio; ii) the concentration of poly(acrylic aid); and iii) the inclusion of (+)-tartaric acid. The above formulation (with x=0.5 g) was studied, water being added in variable amounts, as follows:

| | Cement Formulation | Biaxial Flexural Strength in MPa (Standard Deviations) |
| --- | --- | --- |
| 1. | 60% PAA; 5% tartaric acid; p:l = 1:1 | 57.73 (4.69) |
| 2. | 60% PAA; 5% tartaric acid; p:l = 2:1 | 65.72 (3.82) |
| 3. | 42% PAA; 12.5% tartaric acid; p:l = 3.1:1 | 79.00 (4.16) |
| 4. | 42% PAA; 5.0% tartaric acid; p:l = 3.1:1 | 77.17 (4.47) |
| 5. | 42% PAA; no tartaric acid; p:l = 3.1:1 | 79.17 (4.80) |

The strengths above are the mean of 6 cement discs stored in water at 37° C. for 72 hours. The results confirm that, as with conventional polyalkenoate cements, higher powder:liquid ratios give improved strengths, and that tartaric acid has no strength-enhancing role in a resin-modified cement.

The optimum polymer (i.e. PAA) concentration in the resin-modified cements is a compromise between the weaker polymer solution preferred for compressive strength in conventional glass-ionomer cements and the more concentrated solution preferred for bond strength. A preferred amount is from 40 to 50%.

Fourteen examples of the compositions of one-component resin-modified light-curable cements are given:

| Example No. | Resin Paste | Cement | Composition Weight Percent | | | Fumed Silica | Biaxial Flexural Strength MPa (Std. Dev.) |
| --- | --- | --- | --- | --- | --- | --- | --- |
| | | | PMDM | Ben.P | DMAEM | | |
| 5A | 1.5 | 1.0 | 0.10 | 0.03 | 0.05 | 0.10 | 83.8(12.9) |
| 6A | 1.5 | 1.0 | 0.05 | 0.03 | 0.05 | 0.50 | 80.9(7.7) |
| 7A | 1.5 | 1.0 | 0.05 | 0.03 | 0.05 | 1.00 | 102.8(12.0) |
| 8A | 1.5 | 1.0 | 0.05 | 0.03 | 0.05 | 2.00 | 98.7(11.8) |

-continued

| Example No. | Resin Paste | Cement | Composition Weight Percent PMDM | Ben.P | DMAEM | Fumed Silica | Biaxial Flexural Strength MPa (Std. Dev.) |
|---|---|---|---|---|---|---|---|
| 9A  | 1.5 | 1.0  | 0.10 | — | 0.05 | 0.67 | 96.5(5.4) |
| 11A | 1.5 | 1.0  | 0.10 | — | 0.05 | 0.67 | 85.4(5.1) |
| 12A | 1.5 | 1.0  | 0.10 | — | —    | 1.50 | 85.5(5.2) |
| 13A | 1.5 | 1.0  | 0.10 | — | —    | 0.90 | 57.8(8.1) |
| 14A | 1.5 | 0.75 | 0.10 | — | —    | 1.00 | 64.3(5.8) |
| 15A | 1.5 | 0.5  | 0.10 | — | —    | 1.00 | 76.7(9.8) |
| 17A | 1.5 | 0.5  | 0.05 | — | 0.03 | 0.50 | 83.0(7.9) |
| 20A | 1.5 | 0.5  | 0.10 | — | 0.05 | 1.00 | 88.1(7.8) |
| 24A | 1.5 | 0.5  | 0.10 | — | 0.08 | 0.50 | 68.9(8.7) |
| 25A | 1.5 | 1.0  | 0.10 | — | 0.08 | 0.05 | 55.7(2.1) |

Note:
Example 20A contains 0.075 g of water. 24A contains 0.04 g water. 25A contains 0.10 g water.
"Cement" refers to an anhydrous cement mix of 30 g of "oxide", for the composition of which see later under "Z61/3 cement precursor mixture", plus 1.5 g of D-tartaric acid and 5.0 g of dried poly (acrylic acid).
PMDM is pyromellitic dianhydride methacrylate.
Ben. P refers to benzoyl peroxide.
DMAEM refers to dimethyl amino ethyl methacrylate.

In the foregoing Examples 5A–25A, the resin had one of the following compositions respectively:

Resin

| Example | Bis-GMA | Urethane Dimethacrylate | 1,6 Hexane Diol Dimethacrylate | Camphor-quinone | DMAEM | Benzoyl peroxide |
|---|---|---|---|---|---|---|
| 5A–8A   | 4.46 | 13.05 | 2.346 | 1.00 | —    | —     |
| 9A, 11A | —    | 13.00 | 2.000 | 0.50 | —    | 0.30  |
| 12A     | —    | 5.00  | 5.000 | 0.10 | 0.10 | 0.20  |
| 13A–15A | —    | 5.00  | 5.000 | 0.10 | 0.55 | 0.20  |
| 17A     | —    | 14.00 | 2.000 | 0.20 | —    | 0.10  |
| 20A–25A | —    | 14.00 | 2.000 | 0.20 | —    | 1.00  |
| B       | —    | 15.00 | 2.000 | 0.20 | —    | 0.100 |

There follows an example according to the invention of a tri-cure cement system. The tri-cure cement utilises three curing routes, as the name suggests. These are: i) acid/base neutralisation; ii) free radical-initiated polymerisation via the decomposition of unstable chemical entities by blue light; and iii) the free radical-initiated auto polymerisation, resulting from the reaction of two pastes packed separately in two packs which are mixed at the time of use.

| Materials | Cement Composition (g) Paste A | Paste B |
|---|---|---|
| Resin Example B | 1.5  | 1.5  |
| cement          | 0.5  | —    |
| PMDM            | 0.05 | 0.05 |
| R709            | 0.50 | 0.75 |
| DMAEM           | 0.03 | 0.03 |

4 days Compressive Strength: 212.3 (7.4) MPa
10 days Compressive Strength: 212.7 (7.8) MPa
Dark cure Working Time (21 C.): 4½ minutes
Dark cure Setting Time (21 C.): 12 minutes Resin Example B is as described above, except that when used in Paste A, it has 0.4 g propamine PLU replacing the benzoyl peroxide. Mixing Pastes A and B brings together the amine and the peroxide, thus initiating free-radical production for the third curing route.

Four further Examples of a single-paste light-cured liner are shown as L11–L15 as follows:

LINER FORMULATIONS

| COMPONENTS | L11 | L12 | L13 | L15 |
|---|---|---|---|---|
| Urethane dimethacrylate: Bis GMA | 2.500 | 2.500 | 2.500 | 2.500 |
| 1,6 Hexane diolmethacrylate | 0.340 | 0.340 | 0.340 | 0.340 |
| TMPT | 0.055 | 0.055 | 0.055 | 0.055 |
| Camphorquinone | 0.017 | 0.071 | 0.017 | 0.017 |
| Benzophenone | 0.017 | 0.017 | 0.017 | 0.017 |
| Quantacure BMS (light-sensitive) | 0.034 | 0.034 | 0.034 | 0.034 |
| 2-dimethyl (aminoethyl) methacrylate (ketone accelerator of free radical production) | 0.042 | 0.042 | 0.042 | 0.042 |
| Pyromellitic dianhydride methacrylate | 0.084 | 0.084 | 0.084 | 0.084 |
| Z61/3 Cement precursor mixture | 2.000 | 2.000 | 3.000 | 2.500 |
| Degussa VP R711 Fumed silica | 0.250 | 0.250 | 0.250 | 0.650 |
| Quantacure EPD (light-sensitive) | 0.084 | 0.084 | 0.084 | 0.084 |
| Silanised Raysorb T-3000 | 2.000 | 2.000 | 1.000 | 2.000 |
| Water | 0.240 | 0.240 | 0.240 | 0.240 |
| Acetone | 0.300 | 0.400 | 0.400 | 0.400 |

-continued

| | LINER FORMULATIONS | | | |
|---|---|---|---|---|
| COMPONENTS | L11 | L12 | L13 | L15 |
| Sodium neutralised poly (acrylic acid) S11 | — | 0.100 | 0.200 | — |
| Sodium fluoride | — | — | — | 0.500 |

Notes:
The methacrylates are the resins and cross-linking monomers that polymerise via the application of light;
The Quantacure chemicals and camphorquinone are the light-sensitive chemicals that are decomposed by the light source;
Raysorb T-3000 is a barium-containing aluminosilicate glass, employed in the cements to achieve enhanced radiopacity;
Z61/3 cement precursor mixture is a zinc fluoride-containing anhydrous powder, whose composition is 822 mg "oxide", 137 mg 35% aqueous solution of poly (acrylic acid) of chain length 75000 and 41 mg tartaric acid, the "oxide" itself being non-reactive with the poly (acrylic acid) and being the result of heat-treating at 1200° C. for 1 hour a well-ground mixture of 127 parts zinc fluoride, 6 parts bentonite, 25.74 parts calcium fluoride, 1.34 parts Keltrol xanthan gum, 0.1 parts Nansa surfactant for assisting dissolution of the gum, 240 parts water and 2.8 parts zinc acetate; bentonite is an aluminosilicate being typically 43.8 parts silica, 9.1 parts alumina, 3.2 parts calcium oxide, 2.5 parts magnesium oxide, 0.9 parts ferric oxide and 1.5 parts sodium oxide.

Samples of L11–L15 were formed into discs open to air and light. 40 seconds' dental blue light was shown on the discs, which were then left to stand for a few minutes. They were then hard with translucent resin-rich layers where the light had impinged and with a core of opaque glass ionomer. These single-paste samples had thus unergone dual-cure, viz. fast light-setting of the resin and slower acid-base setting of the glass ionomer. The averaged cumulative fluoride release from L11 and L15 formed into discs and suspended in buffered dilute acetic acid was:

| Cement | micrograms/millimeter squared | |
|---|---|---|
| Age (hours) | L11 | L15 |
| 1 | 0.006 | 0.312 |
| 2 | 0.012 | 0.448 |
| 3 | 0.018 | 0.503 |
| 4 | 0.021 | 0.571 |
| 5 | 0.024 | 0.571 |
| 6 | 0.027 | 0.629 |
| 24 | 0.083 | 0.838 |
| 48 | 0.089 | 0.956 |
| 72 | 0.095 | 1.039 |
| 96 | 0.152 | 1.114 |
| 168 | 0.309 | 1.211 |

Comparing L11 with L15, it may be noted that sodium was introduced into the Liner composition in the form of the sodium neutralised poly (acrylic acid), S11. Sodium encourages the release of fluoride ions from cements in its role as a univalent mobile counter-ion, maintaining electroneutrality.

I claim:

1. A process for making a polyalkenoate cement, comprising mixing an aluminosilicate oxide powder with an aqueous solution comprising polyalkenoic acid, characterised in that the oxide powder has a layer of zinc oxide deposited on it by heat-treating a mixture of aluminosilicate and zinc oxide constituents or precursors thereof.

2. A process according to claim 1, wherein the aluminosilicate oxide further comprises an alkaline earth.

3. A process according to claim 2, wherein the alkaline earth is present in a quantity which would be, at least locally, insufficient by itself to form an acid-degradable glass with the aluminium and silicon.

4. A process according to claim 2, wherein the alkaline earth is wholly or mainly calcium.

5. A process according to claim 1, wherein the said zinc oxide constituent is zinc oxide, which may comprise before the heat treatment a proportion of zinc acetate as a precursor of zinc oxide.

6. A process according to claim 1, wherein the said aluminosilicate oxide constituent is an aluminosilicate clay.

7. A process according to claim 1, wherein the polyalkenoic acid is a poly(carboxylic acid) of molecular weight of the order of $10^4$–$10^6$.

8. A process according to claim 7, wherein the poly (carboxylic acid) is in the form of a copolymer with, or is, poly(vinyl phosphonic acid), and fluoride is present in the oxide powder.

9. A process according to claim 1, wherein the setting of the cement is speeded by a chloride salt of a multivalent cation.

10. A two-part pack for making a polyalkenoate cement, comprising an aluminosilicate oxide powder having a layer of zinc oxide deposited on it, made by heat-treating a mixture of aluminosilicate and zinc oxide constituents or precursors thereof; a polyalkenoic acid or a precursor which forms a polyalkenoic acid upon hydration; and water, wherein the one part contains one of the foregoing constituents and the other part contains the remainder, such that the two parts upon being mixed form a cement.

11. An airtight opaque pack for a light-curable cement, containing: an aluminosilicate oxide powder having a layer of zinc oxide deposited on it, made by heat-treating a mixture of aluminosilicate and zinc oxide constituents or precursors thereof, fluoride; an aqueous polyalkenoic acid such that in the absence of light and air, the foregoing components equilibrate without setting; a curable resin; a cross-linking monomer; and a light-sensitive initiator.

12. A pack according to claim 11, wherein the weight ratio resin:monomer is from 6.5:1 to 7.5:1.

13. A pack according to claim 11, wherein the proportion of the light-sensitive initiator to the total contents is from 1 to 5 weight %.

14. A pack according to claim 11, wherein the proportion of the resin to the total contents exceeds 50 weight %.

15. A pack according to claim 10, wherein the oxide further comprises an alkaline earth.

16. A pack according to claim 15, wherein the alkaline earth is present in a quantity which would be, at least locally, insufficient by itself to form an acid-degradable glass with the aluminium and silicon.

17. A pack according to claim 15, wherein the alkaline earth is wholly or mainly calcium.

18. A pack according to claim 10, wherein the said zinc oxide constituent is zinc oxide, which may comprise before the heat treatment a proportion of zinc acetate as a precursor of zinc oxide.

19. A pack according to claim 10, wherein the said aluminosilicate oxide constituent is an aluminosilicate clay.

20. A pack according to claim 10, further comprising a chloride salt of a multivalent cation.

21. A pack according to claim 10, wherein the polyalkenoic acid is a poly(carboxylic acid) of molecular weight of the order of $10^4$–$10^6$.

22. A glass comprising the atoms Al; Si; Ca and/or Mg; and Zn, wherein Si:Al>1.5:1, and wherein a zinc oxide layer is deposited on the glass.

23. A cement made by a process according to claim 1, or by mixing the two parts of a two-part pack as defined above (excluding 11 to 14), or by opening and exposing to air and light the contents of a pack as defined above.

24. A cement according to claim 23, wherein, in the process, the oxide is a glass as defined above.

* * * * *